US00PP32528P2

(12) United States Plant Patent
Heuger

(10) Patent No.: US PP32,528 P2
(45) Date of Patent: Nov. 24, 2020

(54) ***HELLEBORUS* PLANT NAMED 'COSEH 5300'**

(50) Latin Name: ***Helleborus* x *ericsmithii* X *Helleborus* x *hybridus***
Varietal Denomination: COSEH 5300

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,773

(22) Filed: Nov. 29, 2019

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 5300', characterized by its upright and mounded plant habit; vigorous growth habit; dark green-colored leaves; freely flowering habit; single purple-colored flowers; and good garden performance.

2 Drawing Sheets

Figure 1:
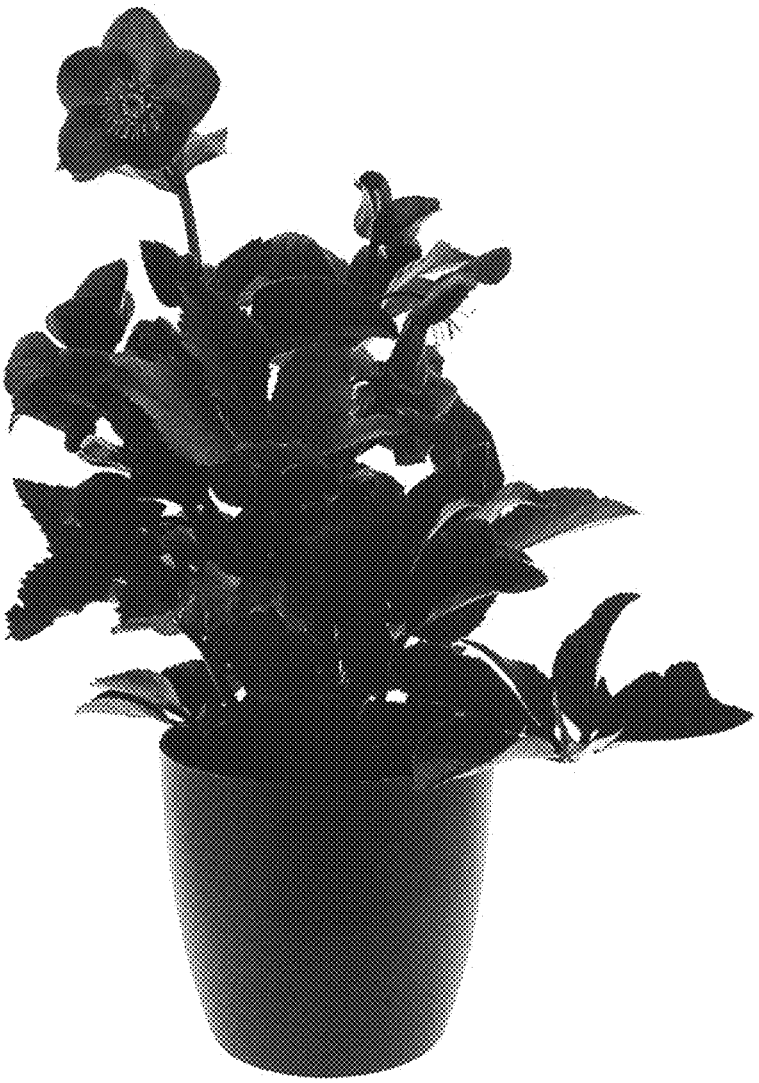

Botanical designation: *Helleborus* x *ericsmithii* X *Helleborus* x *hybridus*.

Cultivar denomination: 'COSEH 5300'.

CROSS-REFERENCED TO CLOSELY-RELATED APPLICATIONS

Title: *Helleborus* Plant Named 'COSEH 5100'
Applicant: Josef Heuger
Filed: Concurrently with the instant application U.S. Plant patent application Ser. No. 16/602,772
Title: *Helleborus* Plant Named 'COSEH 5200'
Applicant: Josef Heuger
Filed: Concurrently with the instant application U.S. Plant patent application Ser. No. 16/602,786
Title: *Helleborus* Plant Named 'COSEH 5400'
Applicant: Josef Heuger
Filed: Concurrently with the instant application U.S. Plant patent application Ser. No. 16/602,792

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 5300'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2011 of a unnamed selection of *Helleborus* x *ericsmithii*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2013.

Asexual reproduction of the new *Helleborus* plant by divisions in a controlled environment in Glandorf, Germany since April, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 5300'. These characteristics in combination distinguish 'COSEH 5300' as a new and distinct *Helleborus* plant:

1. Upright and mounded plant habit.
2. Vigorous growth habit.
3. Dark green-colored leaves.
4. Freely flowering habit.
5. Single purple-colored flowers.
6. Good garden performance.

Plants of the new *Helleborus* differ from plants of the female parent selection in the following characteristics:

1. Plants of the new *Helleborus* are taller than plants of the female parent selection.
2. Plants of the new *Helleborus* have purple-colored flowers whereas plants of the female parent selection have cream-colored flowers.

Plants of the new *Helleborus* differ from plants of the male parent selection in the following characteristics:

1. Plants of the new *Helleborus* are taller than plants of the male parent selection.
2. Plants of the new *Helleborus* have darker green-colored leaves than plants of the male parent selection.

Plants of the new *Helleborus* can be compared to plants of *Helleborus* x *ericsmithii* X *Helleborus* x *hybridus* 'COSEH 5100', disclosed in a U.S. Plant Patent application filed concurrently. Plants of the new *Helleborus* differ primarily from plants of 'COSEH 5100' in flower color as plants of the new *Helleborus* have purple-colored flowers whereas plants of 'COSEH 5100' have light yellow green and red purple to greyed purple bi-colored flowers.

Plants of the new *Helleborus* can be compared to plants of *Helleborus* x *ericsmithii* X *Helleborus* x *hybridus* 'COSEH 5200', disclosed in a U.S. Plant Patent application filed concurrently. Plants of the new *Helleborus* differ primarily from plants of 'COSEH 5200' in growth and flowering habit as plants of the new *Helleborus* are more vigorous and more freely flowering than plants of 'COSEH 5200'.

Plants of the new *Helleborus* can be compared to plants of *Helleborus* x *ericsmithii* X *Helleborus* x *hybridus* 'COSEH 5400', disclosed in a U.S. Plant Patent application filed concurrently. Plants of the new *Helleborus* differ primarily from plants of 'COSEH 5400' in flower color as plants of the new *Helleborus* have purple-colored flowers whereas plants of 'COSEH 5400' have white and red purple bi-colored flowers.

Plants of the new *Helleborus* can also be compared to plants of *Helleborus* x *hybridus* 'Anna's Red', disclosed in U.S. Plant Pat. No. 24,720 (known as 'ABCRD02', also known as 'Anna's Red'. In side-by-side comparisons, plants of the new *Helleborus* differ primarily from plants of 'Anna's Red' in the following characteristics:

1. Leaves of plants of the new *Helleborus* have less distinct venation than leaves of plants of 'Anna's Red'.
2. Plants of the new *Helleborus* flower earlier than plants of 'Anna's Red'.
3. Flowers of plants of the new *Helleborus* are purple-colored whereas flowers of plants of 'Anna's Red' are red in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 5300' grown in a container.

Figure 2:
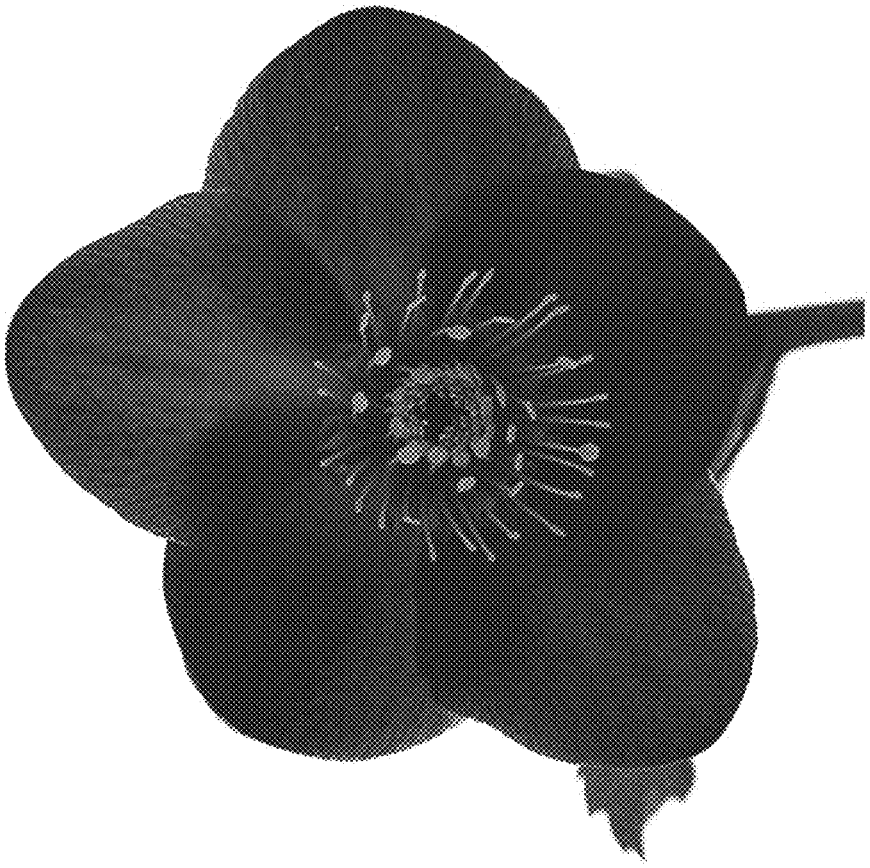

The photograph on the second sheet (FIG. 2 of 2) is a close-up view of a typical flower of 'COSEH 5300'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 5300'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, roughly flattened globular; moderately vigorous to vigorous growth habit and rapid growth rate.

*Plant height, soil level to top of foliar plane*.—About 27.8 cm.

*Plant height, soil level to top of flowers*.—About 41 cm.

*Plant diameter* (*area of spread*).—About 46.8 cm.

Leaf description:

*Arrangement*.—Leaves arranged in a basal rosette; leaves palmately compound with typically five leaflets per leaf.

*Leaf length*.—About 16.1 cm.

*Leaf width*.—About 19.1 cm.

*Leaflet length*.—About 11 cm.

*Leaflet width*.—About 5.8 cm.

*Leaf shape*.—Palmate; reniform in outline.

*Leaflet shape*.—Ovate to obovate.

*Leaflet apex*.—Acute.

*Leaflet base*.—Attenuate.

*Leaflet margin*.—Serrate; slightly undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to 137B; midvein, close to 187C. Developing leaflets, lower surface: Close to 147B strongly dotted and blotched with close to 187A; midvein, close to 187A. Fully developed leaflets, upper surface: Close to darker than between 147A and N189A; venation, close to 147B. Fully developed leaflets, lower surface: Close to 143B and towards the base, close to 200C; venation, close to 152B.

*Petioles*.—Length: About 14.4 cm. Diameter: About 5 mm to 6 mm. Strength: Strong. Texture and luster, upper and lower surfaces: Smooth, glabrous; slightly to moderately glossy. Color, upper and lower surfaces: Close to 146B; densely covered with fine dots, close to 200D and proximally, closer to 200B to 200C.

Flower description:

*Flower shape and habit*.—Single rotate flowers; flowers slightly to moderately cupped; arranged solitary or in clusters with about ten flowers each; freely flowering habit with about 20 flowers developing per plant; flowers facing outwardly to slightly nodding.

*Fragrance*.—None detected.

*Natural flowering season*.—Plants begin flowering about ten months after planting; plants flower during the late autumn into the winter in Germany.

*Flower longevity on the plant*.—About three to four months; sepals persistent, other flower parts are not persistent.

*Flower buds*.—Length: About 2.1 cm. Diameter: About 1.4 cm. Shape: Ovate to oblong. Texture and luster: Smooth, glabrous; matte. Color: Close to 182D; venation, close to 184B and 184C.

*Inflorescence height*.—About 43 cm.

*Inflorescence diameter*.—About 21.6 cm.

*Flower diameter*.—About 9 cm by 9 cm.

*Flower depth* (*height*).—About 2.9 cm.

*Petals*.—All petals are transformed into nectaries.

*Sepals*.—Quantity and arrangement: About five, arranged in a single whorl. Length: About 4.5 cm. Width: About 4.1 cm. Shape: Broadly obovate to broadly elliptic, slightly concave. Apex: Obtuse. Base: Truncate to rounded and cuneate. Margin: Entire; not undulate. Texture and luster, upper and lower surfaces: Smooth, glabrous; matte. Color: When opening, upper surface: Close to 186B and 186C and distally, close to 186A and 186B to 186C. When opening, lower surface: Close to 186B to 186C and distally, close to 186A; venation, close to 59C. Fully opened, upper surface: Close to N77B and proximally, close to 186A; with development, close to N77A and proximally, close to N77A to N77B. Fully opened, lower surface: Close to between N77B and 186A and proximally, close to 186B; with development, close to N77A and proximally, close to between N77A and N186D.

*Flower bracts*.—Quantity per flower: Typically one or two. Length: About 9.8 cm. Width: About 5.6 cm. Shape: Ovate to broadly ovate. Apex: Acute. Base: Truncate. Margin: Distally, serrate and proximally, entire; coarsely undulate. Color, upper surface: Close to 139A; venation, close to 187A. Color, lower surface: Close to 147B; venation, close to 187A.

*Peduncles*.—Length: About 34 cm. Diameter: About 7 mm to 8 mm. Aspect: About 10° from vertical. Strength: Strong. Texture and luster: Smooth, glabrous; slightly glossy. Color: Close to 146C; heavily and finely dotted, close to 200C.

*Pedicels*.—Length: About 4.2 cm. Diameter: About 3 mm. Aspect: About 15° from peduncle axis. Strength: Moderately strong. Texture and luster: Smooth, glabrous; moderately glossy. Color: Close to 174D, densely and finely dotted with close to 182D and 200D.

*Reproductive organs*.—Stamens: Quantity per flower: About 100. Filament length: About 2 cm. Filament color: Close to NN155C, distally, close to 69C. Anther shape: Double and broadly reniform; basifixed. Anther size: About 2 mm by 2 mm. Anther color: Close to 150C. Pollen amount: Moderate. Pollen color: Close to 4D. Pistils: Quantity per flower: About three to seven. Pistil length: About 1.3 cm. Stigma diameter: About 0.3 mm. Stigma shape: Club-shaped. Stigma color: Close to 150D. Style length: About 1.15 cm. Style color: Close to 184B. Ovary color: Close to 183C to 183D. Nectaries (transformed petals): Quantity per flower: About 13. Length: About 1.3 cm. Diameter: About 4 mm. Shape: Tubular, flattened. Texture and luster, inner and outer surfaces: Smooth, glabrous; slightly glossy. Color, immature, inner and outer surfaces: Close to N144D, distally, close to 152A. Color, mature, inner and outer surfaces: Close to 146D, distally, close to 153D and proximally, close to 152B; with development, close to 146D, distally, close to 153B and proximally, close to 152B.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 5300' as illustrated and described.

* * * * *